United States Patent
Keating et al.

(10) Patent No.: US 7,980,694 B2
(45) Date of Patent: Jul. 19, 2011

(54) FUNCTIONAL IMAGING OF THE RETINA

(75) Inventors: David Keating, Glasgow (GB); Stuart Parks, Glasgow (GB)

(73) Assignee: Greater Glasgow Health Board (GB)

( * ) Notice: Subject to any disclaimer, the term of this patent is extended or adjusted under 35 U.S.C. 154(b) by 96 days.

(21) Appl. No.: 12/305,319

(22) PCT Filed: Jun. 19, 2007

(86) PCT No.: PCT/GB2007/002282
§ 371 (c)(1),
(2), (4) Date: Dec. 17, 2008

(87) PCT Pub. No.: WO2007/148073
PCT Pub. Date: Dec. 27, 2007

(65) Prior Publication Data
US 2009/0128776 A1     May 21, 2009

(30) Foreign Application Priority Data
Jun. 19, 2006 (GB) .................. 0612096.8

(51) Int. Cl.
*A61B 3/14* (2006.01)
*A61B 3/00* (2006.01)
(52) U.S. Cl. .......... 351/206; 351/246
(58) Field of Classification Search ........... 351/206, 351/221
See application file for complete search history.

(56) References Cited

U.S. PATENT DOCUMENTS

| | | | |
|---|---|---|---|
| 4,846,567 A | 7/1989 | Sutter | |
| 6,478,424 B1 * | 11/2002 | Grinvald et al. | 351/206 |
| 2005/0122475 A1 * | 6/2005 | Vilser et al. | 351/221 |
| 2005/0288565 A1 * | 12/2005 | Kerr | 600/340 |
| 2007/0091265 A1 * | 4/2007 | Kardon et al. | 351/206 |
| 2007/0188707 A1 | 8/2007 | Nanjo | |
| 2009/0163982 A1 * | 6/2009 | deCharms | 607/89 |

FOREIGN PATENT DOCUMENTS

| | | |
|---|---|---|
| DE | 202005006466 U1 | 6/2005 |
| WO | 2004012576 A2 | 2/2004 |

OTHER PUBLICATIONS

Keating D et al: "The multifocal ERG: unmasked by selective cross-correlation," Vision Research Elsevier UK, vol. 42, No. 27, Dec. 2002, pp. 2959-2968, XP002455285; ISSN: 0042-6968.
Srinivasan V J et al: "In vivo measurement of retinal physiology with high-speed ultrahigh-resolution optical coherence tomography", Optics Letters Opt. Soc. America USA, vol. 31, No. 15, May 19, 2006, pp. 2308-2310, XP002455286, ISSN: 0146-9592.
Bizheva K et al: "Optophysiology: depth-resolved probing of retinal physiology with functional ultrahigh-resolution optical coherence tomography", Proceedings of the National Academy of Sciences of the United States of American, National Academy of Sciences of the United States of America USA, vol. 103, No. 13, Mar. 28, 2006, pp. 5066-5071, XP002455287, ISSN: 0027-8424.

* cited by examiner

*Primary Examiner* — Jordan M. Schwartz
(74) *Attorney, Agent, or Firm* — Workman Nydegger

(57) ABSTRACT

An apparatus and a method for obtaining, in vivo, a measurement of retinal response to an optical stimuli. Light sources provide optical stimuli to the retina in accordance with predetermined stimulation sequences, and images of the retina are obtained and correlated with the predetermined stimulation sequences so as to determine responses of the retina to the optical stimuli. In one particular embodiment, optical stimuli are provided according to m-sequences and correlated with corresponding optical coherence tomography images to determine a functional response of the retina.

18 Claims, 2 Drawing Sheets

FUNCTIONAL IMAGING OF THE RETINA

BACKGROUND

The present invention relates to an apparatus and a method for obtaining functional images of the retina, in particular, an apparatus and a method for obtaining, in vivo, a measurement of retinal response to a visual stimulus.

Electrophysiology studies the electrical properties of tissues and cells by measurement of changes in potential differences or of the flow of electrical currents therein.

In the field of ophthalmology, electroretinograms (ERGs) are used to measure the electrical response of the retina to visual stimuli. An ERG is a measurement of the electrical response of the retina to a full field sensory stimulus and is a triphasic waveform which carries information about the behaviour of various cell types in the retina. It is a composite global response generated by different cellular mechanisms, for example, those of the light sensitive rods and cones and the ganglion cells.

An ERG is obtained by placing electrodes on the cornea and on the skin adjacent to the eye, and measuring the electrical signal which is produced in response to a stimulus as a function of time. ERGs may be used in the diagnosis of retinal diseases such as retinitis pigmentosa and congenital stationary night blindness.

This method has a number of drawbacks. Firstly, it is generally uncomfortable to place electrodes on the cornea of a patient. Furthermore, because physical contact with the eye is necessary, the procedure must be carried out in a hospital environment and is therefore not a service suitable for general optical practitioners, such as high street opticians, to provide. Also, as the method uses a non-localised stimulus, the response measured is a bulk response of the retina as a whole from which it would be difficult to obtain accurate information about specific locations on the retina.

Multifocal ERG uses a number of distinct stimulus sequences to stimulate different regions of the retina simultaneously. As each sequence is distinct, the response for each region may be determined by cross-correlation of the known distinct stimulus sequences with a measurement from a single corneal electrode.

U.S. Pat. No. 4,846,567 describes a multifocal ERG technique in which identical, time-shifted, maximum length sequences (m-sequences) are used to visually stimulate the retina. Electrical signals are measured by means of an electrode placed on the eye, and the measured electrical signals correlated with the m-sequences to determine an electrical response for each m-sequence. The benefit of using m-sequences is that multiple time shifted versions of the same sequence can run simultaneously and enable the recovery of very small signals from multiple retinal sites.

However, this technique suffers in that it still requires the use of an electrode placed on the cornea to measure the electrical response.

It is therefore an object of the present invention to provide a method and an apparatus that obviates and mitigates one or more of the disadvantages and limitations of the prior art.

SUMMARY

According to a first aspect of the present invention, there is provided an apparatus for obtaining images of a retina, the apparatus comprising:

one or more light sources adapted to provide one or more optical stimuli to the retina in accordance with one or more predetermined stimulation sequences;

one or more imaging means adapted to obtain one or more images of the retina; and one or more processing means adapted to correlate the one or more images of the retina with the one or more predetermined stimulation sequences so as to determine one or more responses of the retina to each of the one or more optical stimuli.

The apparatus may therefore determine one or more responses using an imaging means which has the benefit of being non-invasive and non-contact. Furthermore, correlating the obtained images with the one or more predetermined stimulation sequences enables the apparatus to determine the individual responses of the retina caused by each of the optical stimuli.

The one or more light sources may include broadband light sources such as ultrabright LEDs, femtosecond lasers or white light sources, or single frequency light sources such as narrowband LEDs, semiconductor lasers or white light sources with appropriate filters applied. Image sources such as cathode ray tubes (CRT) or liquid crystal display (LCD) devices may also be employed.

Preferably, the one or more light sources are adapted to simultaneously provide one or more optical stimuli to the retina in accordance with the one or more predetermined stimulation sequences.

Accordingly, a number of responses may be determined in one measurement, thereby reducing the amount of time required to determine multiple responses.

Preferably, the one or more light sources are adapted to provide an optical stimulus to separate locations on the retina.

A number of responses may be determined in one measurement which correspond to a number of different locations on the retina, rather than a bulk measurement where pinpointing particular areas is difficult.

Preferably, the one or more light sources comprises a two-dimensional array of a plurality of light sources.

This means that the one or more light sources may be fixed in position with respect to one another, and the signals for each stimuli can be attributed accordingly.

Preferably, the one or more light sources comprises an organic light emitting diode display.

An organic light emitting diode (OLED) display is flexible and may be designed to conform to the specific requirements of the intended application. They may also produce high resolution images, and require no additional light source. It is envisaged that an OLED display may be used to provide stimulation in varying colours and intensities.

Optionally, the one or more predetermined stimulus sequences comprise one or more pseudo-random binary sequences.

Preferably, the one or more pseudo-random binary sequences comprise substantially all possible binary values.

The pseudo-random binary sequences preferably comprise all binary values which are possible within the parameters of the sequence, e.g. length. Generated typically by a number n of shift registers, such sequences are of length $2^n-1$.

Preferably, the one or more predetermined stimulus sequences comprise one or more m-sequences.

M-sequences are useful for determining impulse responses, impart more energy to the retina because they are longer than standard sequences, and also result in a higher signal to-noise ratio. They are also spectrally flat.

Preferably, the one or more predetermined stimulus sequences comprise a plurality of m-sequences overlapping by a predetermined temporal overlap.

Alternatively, the one or more predetermined stimulus sequences comprise a plurality of m-sequences staggered by a predetermined temporal spacing.

Preferably, the one or more predetermined stimulus sequences comprise a plurality of substantially identical m-sequences overlapping by a predetermined temporal overlap.

Alternatively, the one or more predetermined stimulus sequences comprise a plurality of substantially identical m-sequences staggered by a predetermined temporal spacing.

Another benefit of the m-sequence is that by their nature multiple identical or near-identical m-sequences can be used, substantially overlapping or spaced in time, and each still remain detectable.

Alternatively, the apparatus further comprises one or more sequence generators adapted to generate the one or more predetermined stimulation sequences.

In this way, particular sequences can be generated depending on the application. Furthermore, suitable m-sequences can be generated dependent on criteria such as maximum measurement time, desired signal to noise etc.

Preferably, at least one of the one or more imaging means is adapted to obtain one or more optical coherence tomography images of the retina.

Obtaining optical coherence tomography (OCT) images provides cross sectional images of the retina which may be cross-correlated with the stimulation sequences in order to determine a structural response of the retina.

Optionally, at least one of the one or more imaging means is adapted to obtain one or more reflectance images of the retina.

Obtaining reflectance images of the retina provides a visual map of the surface of the retina which may also be compared with or correlated with the stimulation sequences. These images may be obtained by scanning laser ophthalmoscopy (SLO) or standard digital colour cameras.

Preferably, the one or more processing means determines the response of the retina to the predetermined stimulation sequences by determining an electrical signal as a function of time.

By determining the electrical signal as a function of time, the apparatus may provide a temporal correlation between the retinal response corresponding to the signal and the stimulation which is known as a function of time.

Preferably, the processing means determines an optical change between at least two of the one or more images.

An optical change in a region of the retina may be the result of underlying physical processes which effect a change in the reflectance properties of retinal cells in that region. This provides a measurement of the functional integrity of the retinal cells.

Preferably, the apparatus further comprises one or more synchronisation means adapted to synchronise the one or more imaging means with the one or more predetermined stimulus sequences.

By ensuring that acquisition of the images is synchronised with the stimulus sequences, each image can be cross-correlated with a particular stimulus sequence event.

According to a second aspect of the present invention, there is provided a method for obtaining images of a retina, the method comprising the steps of:
(a) providing one or more optical stimuli to the retina in accordance with one or more predetermined stimulation sequences;
(b) obtaining one or more images of the retina; and
(c) correlating the one or more images of the retina with the one or more predetermined stimulation sequences; and
(d) determining one or more responses of the retina to each of the one or more optical stimuli.

The method determines one or more responses using an imaging means which has the benefit of being non-invasive and non-contact. Furthermore, correlating the obtained images with the one or more predetermined stimulation sequences determines the individual responses of the retina due to each of the optical stimuli.

The optical stimuli may be provided by broadband light sources such as ultrabright LEDs, femtosecond lasers or white light sources, or single frequency light sources such as narrowband LEDs, semiconductor lasers or white light sources with appropriate filters applied. Image sources such as cathode ray tubes (CRT) or liquid crystal display (LCD) devices may also be employed.

Preferably, the one or more optical stimuli are provided simultaneously to the retina in accordance with the one or more predetermined stimulation sequences.

A number of responses can thus be determined in one measurement, reducing the amount of time required to determine multiple responses.

Preferably, the step of providing one or more optical stimuli comprises providing one or more optical stimuli to separate locations on the retina.

A number of responses can be determined in one measurement which corresponds to a number of different locations on the retina.

Preferably, the step of providing one or more optical stimuli comprises providing one or more optical stimuli to the retina in accordance with one or more m-sequences.

M-sequences are useful for determining impulse responses, impart more energy to the retina because they are longer than standard sequences, and result in a higher signal to noise ratio.

Preferably, the step of providing one or more optical stimuli comprises separating each of the one or more m-sequences by a predetermined temporal spacing.

Another benefit of the m-sequence is that by their nature multiple identical m-sequences can be used, spaced in time, and each still remain detectable.

Alternatively, the method further comprises the step of generating the one or more predetermined stimulation sequences.

In this way, particular sequences can be generated depending on the application. Furthermore, suitable m-sequences can be generated dependent on criteria such as maximum measurement time, desired signal to noise etc.

Preferably, the step of obtaining one or more images comprises obtaining one or more optical coherence tomography images of the retina.

Obtaining optical coherence tomography (OCT) images provides cross sectional images of the retina which may be cross-correlated with the stimulation sequences in order to determine a structural response of the retina.

Optionally, the step of obtaining one or more images comprises obtaining one or more reflectance images of the retina.

Obtaining reflectance images of the retina provides a visual map of the surface of the retina which may also be compared with or correlated with the stimulation sequences. These images may be obtained by scanning laser ophthalmoscopy (SLO) or standard digital colour cameras.

Preferably, the step of determining the response of the retina to each of the one or more optical stimuli comprises determining an electrical signal as a function of time.

By determining the electrical signal as a function of time, the apparatus may provide a temporal correlation between the retinal response corresponding to the signal and the stimulation which is known as a function of time.

Preferably, the step of determining the response of the retina to each of the one or more optical stimuli comprises determining an optical change between at least two of the one or more images.

An optical change in a region of the retina may be the result of underlying physical processes which effect a change in the reflectance properties of retinal cells in that region. This provides a measurement of the functional integrity of the retinal cells.

Preferably, the method further comprises the step of synchronising the one or more imaging means with the one or more predetermined stimulus sequences.

By ensuring that acquisition of the images is synchronised with the stimulus sequences, each image can be cross-correlated with a particular stimulus sequence event.

According to a third aspect of the present invention, there is provided a module for processing images of a retina, the module comprising:
- image input means adapted to receive one or more images of the retina;
- sequence input means adapted to receive one or more sequences corresponding with the one or more images of the retina; and
- one or more processing means adapted to correlate the one or more images of the retina with the one or more sequences so as to determine one or more responses of the retina to each of the one or more optical stimuli.

The module may be incorporated into existing systems so as to allow them to take advantage of the present invention.

Preferably, the processing means determines an optical change between at least two of the one or more images.

Preferably, the processing means determines an optical change between at least two of the one or more images as a function of time.

An optical change in a region of the retina may be the result of underlying physical processes which effect a change in the reflectance properties of retinal cells in that region. This provides a measurement of the functional integrity of the retinal cells. Additionally, determining this change as a function of time provides temporal information which can be correlated with the one or more sequences.

According to a fourth aspect of the present invention there is provided at least one computer program comprising program instructions, which, when loaded into at least one computer, constitutes the one or more processing means of the first aspect.

According to a fifth aspect of the present invention there is provided at least one computer program comprising program instructions, which, when loaded into at least one computer, constitutes the one or more processing means of the third aspect.

According to a sixth aspect of the present invention there is provided at least one computer program comprising program instructions, which, when loaded into at least one computer, cause the at least one computer to perform the method of according to the second aspect.

Preferably the computer programs are embodied on a recording medium or read-only memory, stored in at least one computer memory, or carried on an electrical carrier signal.

BRIEF DESCRIPTION OF THE DRAWINGS

The present invention will now be described by way of example only and with reference to the accompanying figures in which.

DETAILED DESCRIPTION

Figure 1:
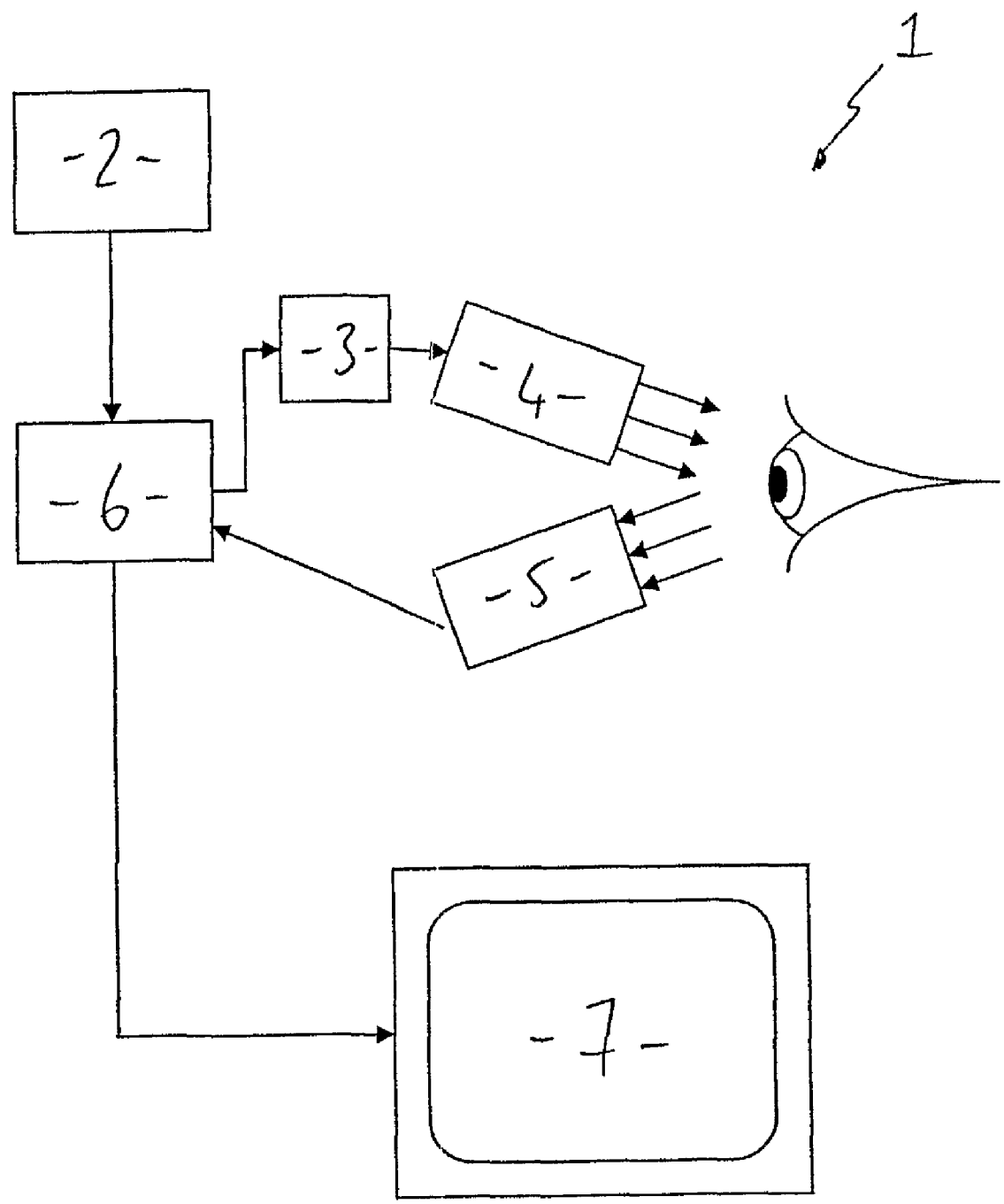
FIG. 1 illustrates in schematic form the acquisition of images of the retina in accordance with an aspect of the present invention.

With reference to FIG. 1, there is presented an apparatus 1 for obtaining functional images of the retina as described in detail below. The apparatus 1 comprises an m-sequence generator 2 which generates maximum length sequences in accordance with predetermined constraints such as required length, desired signal to noise ratio or maximum measurement time. The generated m-sequence is transferred to a control system 3 which converts the binary m-sequence into an output which drives the optical output array 4.

The optical output array 4 comprises a large number of light sources which are each driven by separate, identical but temporally staggered, m-sequences. In this example, the output array is an OLED display adapted to illuminate the retina in nineteen distinct groupings (see for example FIG. 2 below).

An optical coherence tomography (OCT) device 5 obtains OCT images (see for example FIG. 3 below) in synchrony with the m-sequences such that each image can be correlated with a specific m-sequence event by the processing means 6. For example, for a known m-sequence, all OCT images where the corresponding optical stimulus was active can be identified and a mean calculated for that particular optical stimulus. As the particular optical stimulus is directed to a particular region of the retina (as in FIG. 2 below), functional information about those regions of the retina can therefore be determined.

The processing means 6 carries out the abovementioned image processing, but also controls the apparatus 1, synchronises the optical stimulation and the image acquisition, as well as providing a visual display 7 for an operator.

It is foreseen that the m-sequence generator 2 may be dispensed with in the eventuality that the maximum length sequences are in fact preset and simply extracted from memory (preferably non-volatile) in the control system 3.

Figure 2:
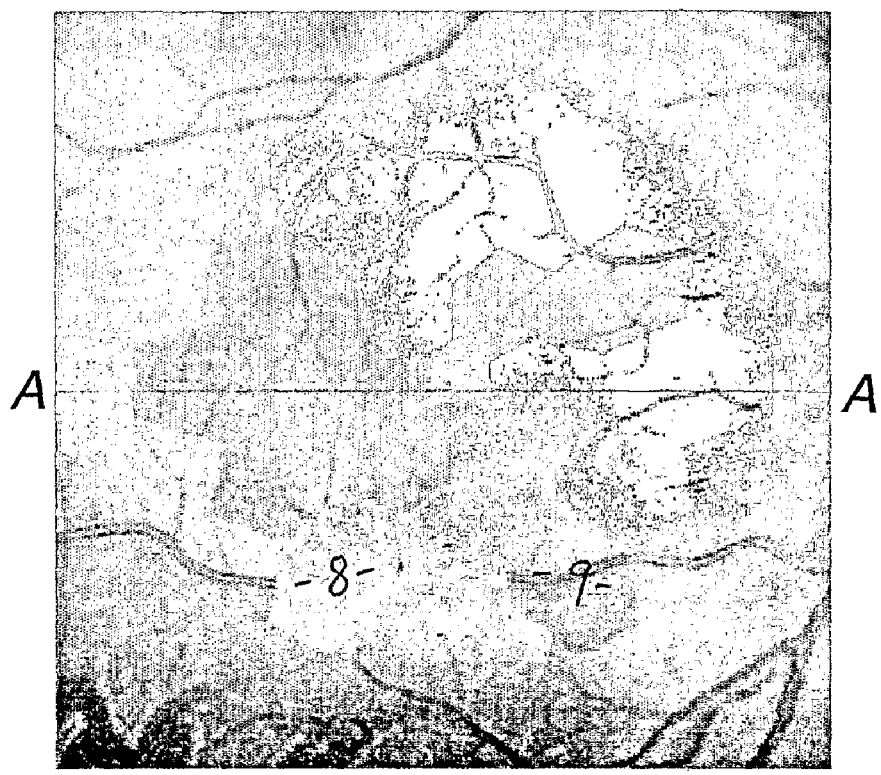
FIG. 2 illustrates a typical stimulation pattern projected onto a retina.

FIG. 2 illustrates the illumination of a retina by the optical output array 4 of FIG. 1. The OLED display effects nineteen distinct areas of illumination, in this example each area is roughly hexagonal. The m-sequences corresponding with each area cause the control system 3 to switch the illumination between an "on" condition (for example, see reference numeral 8) and an "off" condition (for example, see reference numeral 9) in that area.

Figure 3:
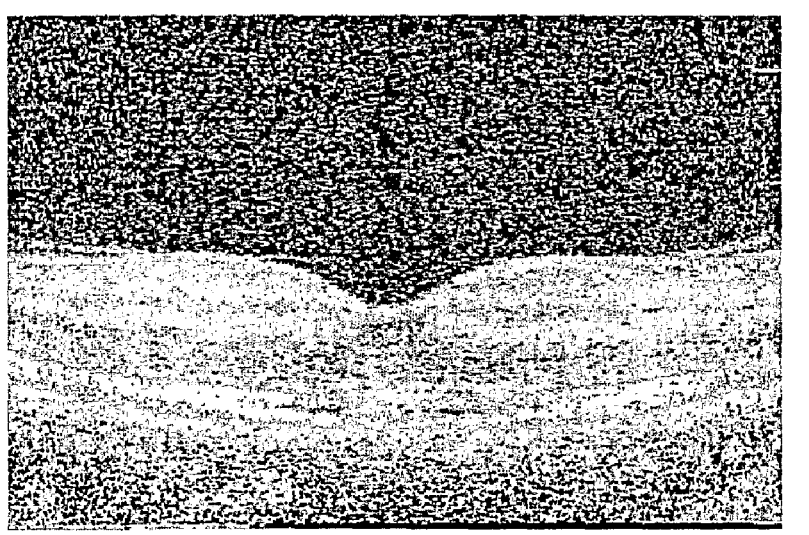
FIG. 3 illustrates a typical optical coherence tomography image of a retina corresponding with that illustrated in FIG. 2.

Simultaneously with each step in the m-sequence the OCT device 5 obtains cross sectional images of the areas of illumination. FIG. 3 illustrates a typical OCT image 10 acquired along line A of FIG. 2. The OCT image 10 is a cross sectional view of the retina and reveals, in high resolution, the structure of the retina. This structure reveals, at a cellular level, the physical reaction of the retina to the optical stimulation.

Obtaining these high resolution images of the retina and cross correlating them with the known m-sequences which provide that optical stimulation allows determination of the physical and hence functional response of the retina to the stimulation.

The present invention allows measurement of the optical response, and hence determination of functional response, at a cellular level. This is achieved by a combination of improved precision and measurement at the cellular level of high resolution cross sectional images.

Using m-sequences results in an improved signal to noise ratio, while maintaining the facility for multiple sequences to be employed (albeit with a time delay between each). Using an m-sequence, the mean of all the images obtained when the stimulus is inactive is subtracted from the mean of all the images obtained when the stimulus is active.

In practice, different frequencies and different intensities of optical stimulation may be used in order to stimulate different cellular structures. For example, red, green and blue stimuli may be employed to test the response of the corresponding cones.

As optical responses can be determined at the cellular level with, for example, OCT images, it may be possible to diagnose conditions which are difficult to recognise with current technology. Changes in the reflectance of the photoreceptor layer may be indicative of diseases such as retinitis pigmentosa or cone dystrophy, and changes in the reflectance of the ganglion cell layer may be symptomatic of glaucoma.

In summary, the apparatus and method of the present invention will allow a general optical practitioner such as an optician to be able to determine the response of a patient's retina to optical stimuli without the discomfort or additional medical supervision required with conventional systems. Furthermore, the structure of the eye can be monitored and correlated with the stimulation.

Other benefits of this system are that it facilitates early diagnosis of retinal and visual defects, and can also monitor these defects over time. Diabetes sufferers may also be monitored over time to spot the early signs of diabetic retinopathy which affects up to 80% of all diabetics who have had the condition over 15 years.

Medical trials, for example on new drugs, may be monitored in the eye as systemic toxicity is evident in the eye. Furthermore, during medical trials side-effects may manifest themselves early on in the eye and monitoring the eye over time using the present invention will allow progress of the side-effects to be recorded.

Further modifications and improvements may be added without departing from the scope of the invention as defined by the appended claims.

The invention claimed is:

1. An apparatus for obtaining images of a retina, the apparatus comprising:
   one or more light sources adapted to provide one or more optical stimuli to separate locations on the retina in accordance with one or more m-sequences;
   one or more imaging means adapted to obtain one or more optical coherence tomography images of the retina; and
   one or more processing means adapted to cross-correlate the one or more optical coherence tomography images of the retina with the one or more m-sequences so as to determine one or more structural responses of the retina to each of the one or more optical stimuli.

2. The apparatus as claimed in claim 1 wherein, the one or more light sources comprises a two-dimensional array of a plurality of light sources.

3. An apparatus as claimed in claim 1 wherein, the one or more m-sequences comprise a plurality of m-sequences overlapping by a predetermined temporal overlap, a plurality of m-sequences staggered by a predetermined temporal spacing, a plurality of substantially identical m-sequences overlapping by a predetermined temporal overlap, or a plurality of substantially identical m-sequences staggered by a predetermined temporal spacing.

4. An apparatus as claimed in claim 1 wherein, the one or more processing means determines the structural response of the retina to the one or more optical stimuli by determining an electrical signal as a function of time.

5. An apparatus as claimed in claim 4 wherein, the apparatus provides a temporal correlation between the retinal response corresponding to the signal and the m-sequences as a function of time.

6. An apparatus as claimed in claim 1 wherein, the apparatus further comprises one or more synchronization means adapted to synchronize the one or more imaging means with the one or more m-sequences.

7. A method for obtaining images of a retina, the method comprising the steps of:
   (a) providing one or more optical stimuli to separate locations on the retina in accordance with one or more m-sequences;
   (b) obtaining one or more optical coherence tomography images of the retina;
   (c) cross-correlating the one or more optical coherence tomography images of the retina with the one or more m-sequences; and
   (d) determining one or more structural responses of the retina to each of the one or more optical stimuli.

8. The apparatus as claimed in claim 1 wherein, the one or more light sources comprises an organic light emitting diode display capable of providing stimuli in varying colours and intensities, or are selected from the group comprising ultrabright LEDs, femtosecond lasers, white light sources, narrowband LEDs, semiconductor lasers, white light sources comprising filters, cathode ray tubes and liquid crystal display devices.

9. An apparatus for obtaining images of a retina, the apparatus comprising:
   one or more light sources adapted to provide one or more optical stimuli to separate locations on the retina in accordance with one or more m-sequences;
   one or more imaging means adapted to obtain one or more reflectance images of the retina, wherein the one or more imaging means comprises a scanning laser opthalmoscope; and
   one or more processing means adapted to cross-correlate the one or more reflectance images of the retina with the one or more m-sequences so as to determine one or more structural responses of the retina to each of the one or more optical stimuli.

10. The apparatus as claimed in claim 9 wherein, the one or more light sources comprises a two-dimensional array of a plurality of light sources.

11. An apparatus as claimed in claim 9 wherein, the one or more m-sequences comprise a plurality of m-sequences overlapping by a predetermined temporal overlap, a plurality of m-sequences staggered by a predetermined temporal spacing, a plurality of substantially identical m-sequences overlapping by a predetermined temporal overlap, or a plurality of substantially identical m-sequences staggered by a predetermined temporal spacing.

12. An apparatus as claimed in claim 9 wherein, the one or more processing means determines the structural response of the retina to the one or more optical stimuli by determining an electrical signal as a function of time.

13. An apparatus as claimed in claim 9 wherein, the apparatus further comprises one or more synchronization means adapted to synchronize the one or more imaging means with the one or more m-sequences.

14. The apparatus as claimed in claim 9 wherein, the one or more light sources comprises an organic light emitting diode display capable of providing stimuli in varying colours and intensities, or are selected from the group comprising ultra-bright LEDs, femtosecond lasers, white light sources, narrowband LEDs, semiconductor lasers, white light sources comprising filters, cathode ray tubes and liquid crystal display devices.

15. A method for obtaining images of a retina, the method comprising the steps of:
   (a) providing one or more optical stimuli to separate locations on the retina in accordance with one or more m-sequences;
   (b) obtaining one or more reflectance images of the retina, wherein obtaining one or more reflectance images of the retina comprises obtaining one or more scanning laser opthalmoscope images of the retina;
   (c) cross-correlating the one or more reflectance images of the retina with the one or more m-sequences; and
   (d) determining one or more structural responses of the retina to each of the one or more optical stimuli.

16. A method as claimed in claim 15, wherein the one or more m-sequences comprise a plurality of m-sequences overlapping by a predetermined temporal overlap, a plurality of m-sequences staggered by a predetermined temporal spacing, a plurality of substantially identical m-sequences overlapping by a predetermined temporal overlap, or a plurality of substantially identical m-sequences staggered by a predetermined temporal spacing.

17. A non-transitory computer readable media having computer-executable instructions stored thereon and configured to implement the method of claim 15 when executed by a computer.

18. A non-transitory computer readable media having computer-executable instructions stored thereon and configured to implement the method of claim 7 when executed by a computer.

* * * * *